United States Patent
Berger et al.

(10) Patent No.: US 6,825,202 B2
(45) Date of Patent: Nov. 30, 2004

(54) ARYLSULFONYL DERIVATIVES WITH 5-HT6 RECEPTOR AFFINITY

(75) Inventors: Jacob Berger, Los Altos Hills, CA (US); Robin Douglas Clark, Lawai, HI (US); Shu-Hai Zhao, Sunnyvale, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 21 days.

(21) Appl. No.: 10/215,769

(22) Filed: Aug. 9, 2002

(65) Prior Publication Data

US 2003/0069254 A1 Apr. 10, 2003

Related U.S. Application Data

(60) Provisional application No. 60/311,504, filed on Aug. 10, 2001, and provisional application No. 60/384,711, filed on May 31, 2002.

(51) Int. Cl.[7] .................. A61K 31/495; A61K 31/496; A61K 31/451; C07D 295/112; C07D 405/10

(52) U.S. Cl. .................. 514/254.11; 514/255.03; 514/317; 514/326; 544/376; 544/377; 544/395; 546/196; 546/197; 546/206; 546/236

(58) Field of Search .................. 544/395, 376–377; 546/236, 196, 197, 206; 514/255.03, 317, 254.11, 326

(56) References Cited

U.S. PATENT DOCUMENTS 5,990,105 A 11/1999 Boes et al.

FOREIGN PATENT DOCUMENTS

| | | |
|---|---|---|
| WO | WO 98/27081 A1 | 6/1998 |
| WO | WO 99/02502 A2 | 1/1999 |
| WO | WO 99/42465 A2 | 8/1999 |
| WO | WO 00/12073 A1 | 3/2000 |
| WO | WO 00/12623 A2 | 3/2000 |
| WO | WO 01/32646 A2 | 5/2001 |
| WO | WO 01/98279 A2 | 12/2001 |

OTHER PUBLICATIONS

Robichaud et al in Annual Reports in medicinal Chemistry, vol. 36, p. 11–20 (2000).*

Rogers et al. Psychopharmacology, vol. 158, p. 114–119 (2001).*

Bromidge, Steven M. et al., "Phenyl Benzenesulfonamides are Novel and Selective 5–HT$_6$ Antagonists: Identification of N–(2,5–Dibromo–3–fluorophenyl)–4–methoxy–3–piperazin–1–ylbenzenesulfonamide (SB–357134)," *Bioorganic & Medicinal Chemistry Letters*, Jan.2001, pp. 55–58, vol. 11, No. 1,8 Pergamon.

Bader, et al., "Antimalarial Compounds Related to Diaminodiphenyl Sulfone," *J. Med. Chem.*, Jul. 1969, pp. 709–710, 12 (4).

Monsma, Jr., et al., "Cloning and Expression of a Novel Serotonin Receptor with High Affinity for Tricyclic Psychotropic Drugs," 1993, pp. 320–327, vol. 43.

* cited by examiner

Primary Examiner—Emily Bernhardt
(74) *Attorney, Agent, or Firm*—Robert C. Hall

(57) ABSTRACT

This invention relates to compounds which have generally 5-HT6 receptor affinity and which are represented by Formula (I):

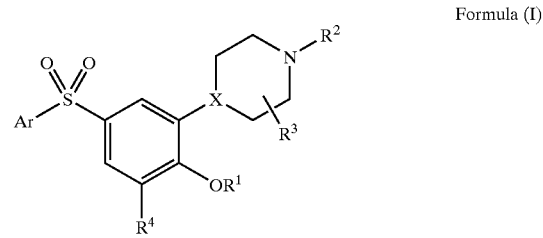

Formula (I)

wherein Ar, $R^1$, $R^2$, $R^3$ or $R^4$ are as defined in the specification, or pharmaceutically acceptable salts or solvates thereof. The invention further relates to pharmaceutical compositions containing such compounds, methods for their use as therapeutic agents, and methods of preparation thereof.

24 Claims, No Drawings

ARYLSULFONYL DERIVATIVES WITH 5-HT6 RECEPTOR AFFINITY

CROSS REFERENCE

This application claims the benefit of priority of U.S. Provisional Patent Applications Ser. No. 60/311,504, filed Aug. 10, 2001, and Ser. No. 60/384,711, filed May 31, 2002, which are incorporated herein by reference in their entirety.

FIELD OF THE INVENTION

This invention relates to new 1-(5-arylsulfonyl-phenyl) piperazine and 4-(5-arylsulfonyl-phenyl)piperidine derivatives with 5-HT6 receptor affinity, and associated pharmaceutical compositions, methods for use as therapeutic agents, and methods of preparation thereof.

BACKGROUND OF THE INVENTION

The actions of the neurotransmitter 5-hydroxytryptamine (5-HT) as a major modulatory neurotransmitter in the brain, are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nerve system disorders. In particular, 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, migraine, Alzheimer's disease (enhancement of cognitive memory), sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. (See for ex. B. L. Roth et al., J. Pharmacol. Exp. Ther.1994, 268, pages 1403–14120, D. R. Sibley et al., Mol. Pharmacol. 1993, 43, 320–327, A. J. Sleight et al, Neurotransmission 1995, 11, 1–5, and A. J. Sleight et al. Serotonin ID Research Alert, 1997, 2 (3), 115–8.

Several arylsulfonyl compounds with 5-HT6 affinity have been disclosed in U.S. Pat. No. 5,990,105 to Bos et al., but it has been surprisingly found that the novel compounds of Formula I possess greater affinity, and therefore would be suitable and highly desirable for the treatment or prevention of central nervous disorders described herein.

SUMMARY OF THE INVENTION

This invention relates to compounds comprising Formula (I):

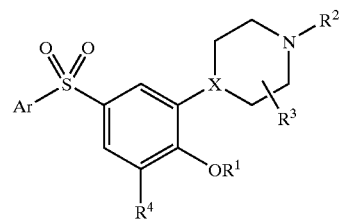

Formula (I)

wherein:
Ar is an optionally substituted aryl group selected from naphthyl or phenyl;
X is —CH— or —N—;
$R^1$ is $(C_1-C_6)$alkyl;
$R^2$ and $R^3$ are each independently in each occurrence hydrogen or $(C_1-C_6)$alkyl, or $R^2$ and $R^3$ together may form a $(C_3-C_4)$alkylene group;
$R^4$ is hydrogen, or $R^1$ and $R^4$ together may form a —CH=CH—, —CH$_2$—CH$_2$—, —CH$_2$—CH$_2$—CH$_2$—, —O—CH$_2$—, or —O—CH$_2$—CH$_2$— group; it is understood that $R^4$ and $OR^1$ together with the phenyl to which they are attached would form a benzofuran, a 2,3-dihydrobenzofuran, a chromane, 2,3-dihydro-benzo[1,4]dioxine, or a benzo[1,3]dioxole ring;

or pharmaceutically acceptable salts or solvates thereof.

In another aspect, the invention relates to pharmaceutical compositions containing a therapeutically effective amount of at least one compound of Formula (I), or individual isomers, racemic or non-racemic mixtures of isomers, or pharmaceutically acceptable salts or solvates thereof, in admixture with at least one suitable carrier.

In another aspect, this invention relates to a method of treatment of a disease in a mammal treatable by administration of compound of Formula (I) having a selective affinity for the 5-HT6 receptor, in particular a method of treatment in a subject having a disease state comprising Alzheimer's disease, central nervous disorders, such as for example, psychoses, schizophrenia, manic depressions, neurological disorders, Parkinson's disease, amyotrophic lateral sclerosis and Huntington's disease. In another aspect, this invention relates to a method of treatment in a subject having a gastrointestinal disease comprising functional bowel disorder.

In a preferred embodiment, the invention further relates to processes for preparing compounds of Formula (I).

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon radical, consisting solely of carbon and hydrogen atoms, having from one to twelve carbon atoms inclusive, unless otherwise indicated. Examples of alkyl radicals include, but are not limited to, methyl, ethyl, propyl, isopropyl, isobutyl, sec-butyl, tert-butyl, pentyl, n-hexyl, octyl, dodecyl, and the like.

"Lower alkyl" means the monovalent linear or branched saturated hydrocarbon radical, consisting solely of carbon and hydrogen atoms, having from one to six carbon atoms inclusive, unless otherwise indicated. Examples of lower alkyl radicals include, but are not limited to, methyl, ethyl, propyl, isopropyl, sec-butyl, tert-butyl, n-butyl, n-pentyl, n-hexyl, and the like.

"Alkoxy" means the radical —O—R, wherein R is a lower alkyl radical as defined herein. Examples of alkoxy radicals include, but are not limited to, methoxy, ethoxy, isopropoxy, and the like.

"Arylsulfonyl" means the radical —$SO_2R$, wherein R is an aryl radical as defined herein. Examples of arylsulfonyl radicals include, but are not limited to, benzenesulfonyl, 3-chlorobenzenesulfonyl, naphthalene-2-sulfonyl, naphthalene-1-sulfonyl, and the like.

"Aryl" means the monovalent cyclic aromatic hydrocarbon radical consisting of one or more fused rings in which at least one ring is aromatic in nature, which can optionally be substituted with hydroxy, cyano, lower alkyl, lower alkoxy, thioalkyl, halo, haloalkyl, hydroxyalkyl, nitro, alkoxycarbonyl, aminosulfonyl, sulfonylamino, and/or trifluoromethyl, unless otherwise indicated. Examples of aryl radicals include, but are not limited to, phenyl, naphth-2-yl, naphth-1-yl, fluorophenyl, dichlorophenyl, and the like.

"Leaving group" means the group with the meaning conventionally associated with it in synthetic organic chemistry, i.e., an atom or group displaceable under alkylating conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen atoms present in the reactants.

"Amino-protecting group" means the protecting group that refers to those organic groups intended to protect the nitrogen atom against undesirable reactions during synthetic procedures and includes, but is not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Optional" or "optionally" means that the subsequently described event or circumstance may but need not occur, and that the description includes instances where the event or circumstance occurs and instances in which it does not. For example, "optional bond" means that the bond may or may not be present, and that the description includes single, double, or triple bonds.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

It should be understood that all references to pharmaceutically acceptable salts include solvent addition forms (solvates) or crystal forms (polymorphs) as defined herein, of the same acid addition salt.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Prodrug" means a pharmacologically inactive form of a compound which must be metabolized in vivo, e.g., by biological fluids or enzymes, by a subject after administration into a pharmacologically active form of the compound in order to produce the desired pharmacological effect. The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Reference to a compound herein includes prodrug forms of a compound.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

"Disease state" means any disease, condition, symptom, or indication.

Throughout the application the following abbreviations are used with the following meaning:

| DMF | N,N-Dimethylformamide |
| --- | --- |
| DMSO | Dimethylsulfoxide |
| Hal | Halogen or halide |
| L | Leaving group |
| opt. | Optionally |
| P | Protective group |
| TFA | Trifluoroacetic acid |
| TFAA | Trifluoroacetic acid anhydride |
| THF | Tetrahydrofuran |

Nomenclature

In general, the nomenclature used in this Application is based on AUTONOM™ v.4.0, a Beilstein Institute computerized system for the generation of IUPAC systematic nomenclature.

For example, a compound of Formula (I) wherein Ar is 3-chlorophenyl, $R^1$ is methyl, $R^2$ and $R^3$ are hydrogen and X is —N—, is named 1-[5-(3-chloro-benzenesufonyl)-2-methoxy-phenyl]-piperazine.

Preferred Compounds

Among compounds of the present invention set forth in the Summary of the Invention, certain compounds of Formula (I), or pharmaceutically acceptable salts or solvates thereof, are preferred:

Ar is optionally substituted naphthyl or phenyl, and preferably optionally substituted naphthyl wherein the substitutents are independently selected from $(C_1-C_6)$alkyl, halogen, haloalkyl, $(C_1-C_6)$alkoxy, cyano, nitro, amino, and alkylsulfonyl, or optionally substituted phenyl, wherein the substituents are independently selected from halogen, haloalkyl, $(C_1-C_6)$alkoxy, cyano, nitro, and alkylsulfonyl.

X is —CH— or —N—, preferably —N—.

$R^1$ is $(C_1-C_6)$alkyl, preferably methyl.

$R^2$ and $R^3$ are each independently in each occurrence hydrogen or $(C_1-C_6)$alkyl, or $R^2$ and $R^3$ together may form a $C_3-C_4$ alkylene; preferably $R^2$ and $R^3$ are hydrogen.

$R^4$ is hydrogen or $R^1$ and $R^4$ together may form a —CH=CH— or —CH$_2$—CH$_2$—, —CH$_2$—CH$_2$—CH$_2$—, —O—CH$_2$—, or —O—CH$_2$—CH$_2$— group; preferably $R^4$ is hydrogen.

Exemplary particularly preferred compounds, or individual isomers, racemic or non-racemic mixtures of isomers, or pharmaceutically acceptable salts or solvates thereof, include:

1-[5-(4-chloro-benzenesulfonyl)-2-methoxy-phenyl]-piperazine,

1-[2-methoxy-5-(4-methoxy-benzenesulfonyl)-phenyl]-piperazine, 1-(5-benzenesulfonyl-2-methoxy-phenyl)-piperazine, 1-[2-methoxy-5-(naphthalene-2-sulfonyl)-phenyl]-piperazine, 1-[5-(3-fluoro-benzenesulfonyl)-2-methoxy-phenyl]-piperazine, 1-[2-methoxy-5-(naphthalene-1-sulfonyl)-phenyl]-piperazine, 1-[5-(3-chloro-benzenesulfonyl)-2-methoxy-phenyl]-piperazine, 1-[5-(4-chloro-benzenesulfonyl)-2-methoxy-phenyl]-4-methyl-piperazine, 1-[5-(4-fluoro-naphthalene-1-sulfonyl)2-methoxyphenyl] piperazine, 1-[5-(3,4-dichloro-benzenesulfonyl)-2-methoxy-phenyl]-piperazine, 1-[2-methoxy-5-(4-methoxy-naphthalene-1-sulfonyl) phenyl]piperazine, 1-[5-(2,4-dichloro-benzenesulfonyl)-2-methoxy-phenyl]-piperazine, or 4-[5-(4-chloro-benzenesulfonyl)-2-methoxy-phenyl]-piperidine.

GENERAL SYNTHETIC REACTION SCHEMES

Compounds of the present invention may be made by the methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. The following synthetic reaction schemes are merely illustrative of some methods by which the compounds of the present invention may be synthesized, and various modifications to these synthetic reaction schemes may be made and will be suggested to one skilled in the art having referred to the disclosure contained in this Application.

The starting materials and the intermediates of the synthetic reaction schemes may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein preferably take place at atmospheric pressure over a temperature range from about −78° C. to about 150° C., more preferably from about 0° C. to about 125° C., and most preferably and conveniently at about room (or ambient) temperature, e.g., about 20° C.

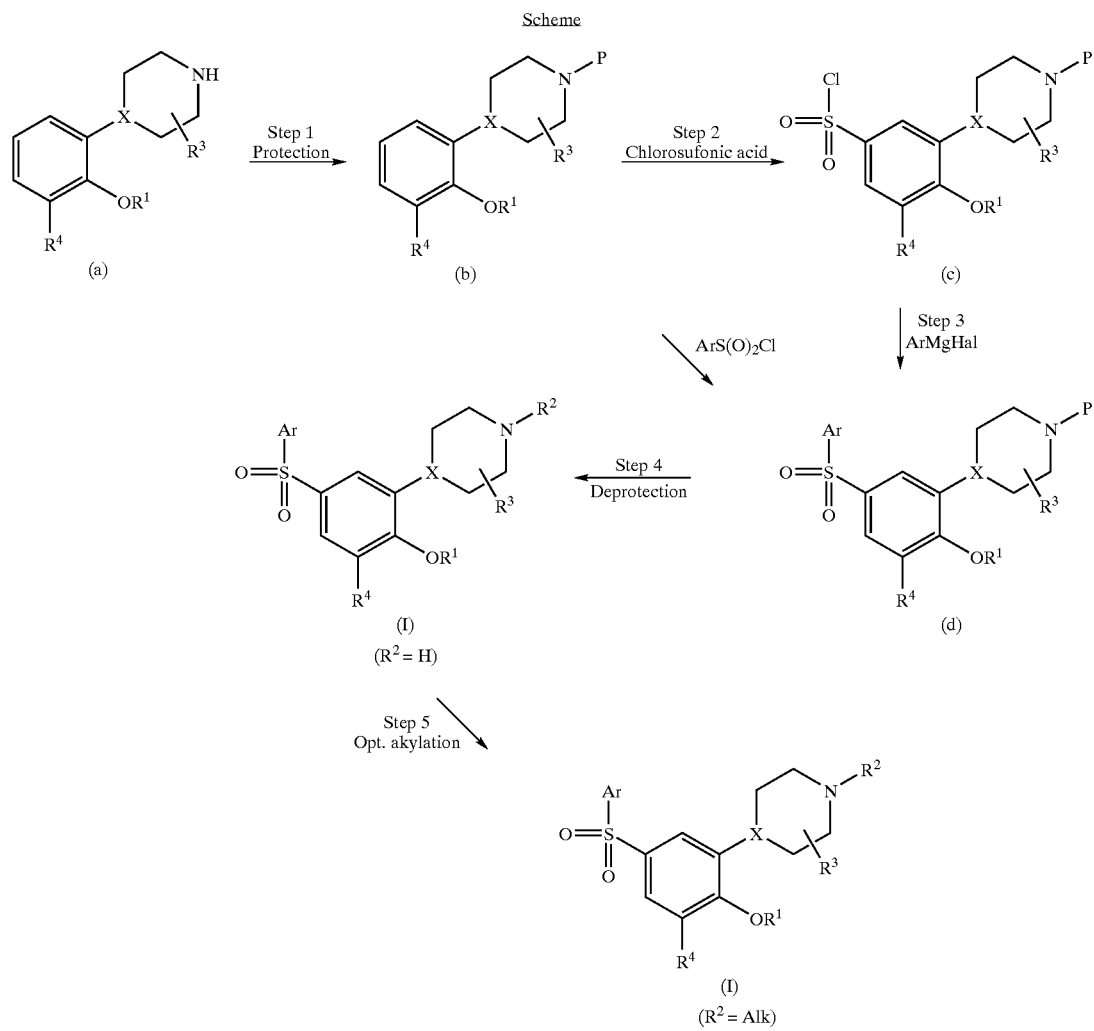

Scheme 1-(2-Methoxy-phenyl)piperazine or 4-(2-methoxyphenyl) piperidine of general Formula (a) can be protected with an acid resistant protecting group, for example trifluoroacetyl, to afford the protected piperazine or piperidine derivatives of general Formula (b). If the compound of Formula (I) wherein $R^2$ is alkyl is desired, alkylation of the nitrogen can be performed at this point or during Step 5 of this scheme. In Step 2, chlorosulfonation of a compound of general Formula (b) can afford the chlorosulfone of Formula (c), that, as shown in Step 3, after treatment with a Grignard reagent of general Formula ArMgHal, wherein the halide (Hal) is preferably a bromide, can afford the protected compound of Formula (d). In Step 4, deprotection with a strong base such as sodium hydroxyde can afford the piperazine or piperidine compound of general Formula (I) wherein $R^2$ is hydrogen. Steps 3 and 4 can be performed sequentially without isolation of the protected compound of Formula (d). In Step 5, if an alkylated piperazine or piperidine compound is desired, alkylation can be performed at this point by methods well known to the one skilled in the art, such as by the Eschweiler-Clarke procedure, i.e. treatment of the secondary amine with formaldehyde and formic acid, or by reaction with an appropriate alkylhalide in the presence of a base.

Alternatively compound of Formula (b) can be reacted by procedures well known in the art with a compound of general Formula $ArSO_2Cl$ to afford the protected compound of Formula (d), which after deprotection can afford a compound of Formula (I), wherein $R^2$ is hydrogen. If the alkylated compound is desired, alkylation can be performed as described herein.

GENERAL UTILITY

The compounds of the invention have selective 5-HT6 receptor affinity and as such are expected to be useful in the treatment of certain CNS disorders such as Parkinson's disease, Huntington's disease, anxiety, depression, manic depression, psychosis, epilepsy, obsessive compulsive disorders, migraine, Alzheimer's disease (enhancement of cognitive memory), sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain GI (gastrointestinal) disorders such functional bowel disorder.

TESTING

The pharmacology of the compounds of this invention was determined by art recognised procedures. The in vitro techniques for determining the affinities of test compounds at the 5-HT6 receptor in radioligand binding and functional assays are described in Example 13.

ADMINISTRATION AND PHARMACEUTICAL COMPOSITION

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavours, stabilising, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavours, stabilisers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilising and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilising agents, dispersing agents, suspending agents, thickening agents, or colouring agents. Formulations suitable for topical administration in the mouth include lozenges comprising active agents in a flavoured base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomising spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurised pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Examples 6–12.

EXAMPLES

The following preparations and examples are given to enable those skilled in the art to more clearly understand and to practice the present invention. They should not be considered as limiting the scope of the invention, but merely as being illustrative and representative thereof.

Example 1

1-[2-Methoxy-4-(naphthalene-1-sulfonyl)-phenyl]-piperazine

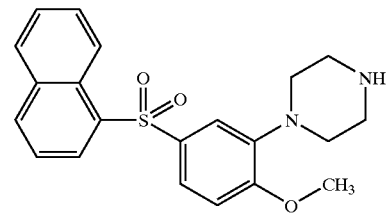

Step 1:
2,2,2-Trifluoro-1-[4-(2-methoxy-phenyl)-piperazin-1-yl]-ethanone

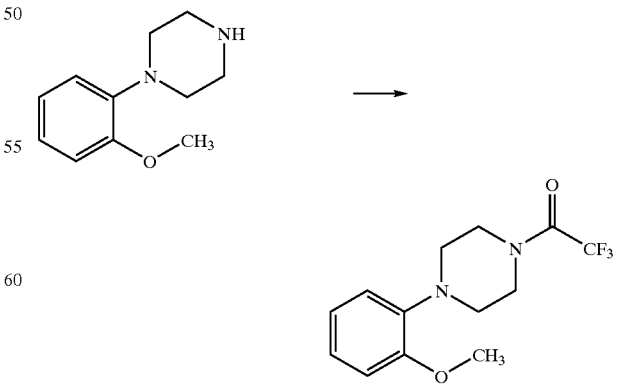

Trifluoroacetic anhydride (23.07 g; 0.11 mol) was added dropwise under nitrogen atmosphere to an ice-cooled solution of 1-(2-methoxyphenyl)piperazine (19.2 g; 0.1 mol) and pyridine (8.85 g; 0.11 mol) in dichloromethane (300 mL). After 1 h at ambient temperature a 10% aqueous HCl solution was added. The layers were separated and the organic phase was washed with water (2×100 mL), dried (Na$_2$SO$_4$) and concentrated to give 2,2,2-trifluoro-1-[4-(2-methoxy-phenyl)-piperazin-1-yl]-ethanone as a light red oil (28 g) which was used in Step 2 without purification.

Similarly following step 1 but replacing 1-(2-methoxyphenyl)piperazine with 4-(2-methoxyphenyl)piperidine, 2,2,2-trifluoro-1-[4-(2-methoxy-phenyl)piperidin-1-yl]ethanone was prepared.

Step 2:

4-Methoxy-3-[4-(2,2,2-trifluoro-acetyl)-piperazin-1-yl]-benzenesulfonyl chloride

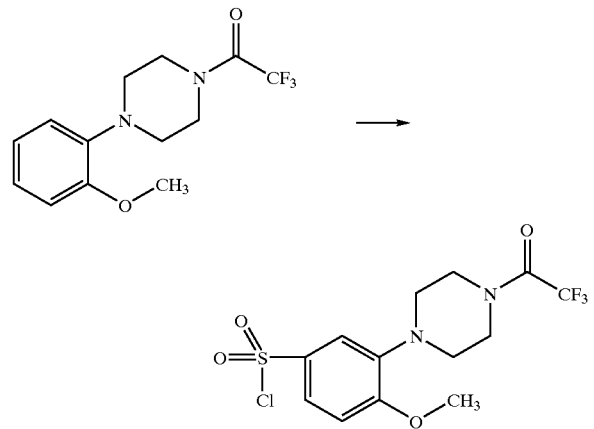

A solution of 2,2,2-trifluoro-1-[4-(2-methoxy-phenyl)-piperazin-1-yl]-ethanone (14 g; 0.48 mol) in dichloromethane (20 mL) was added to chlorosulfonic acid (75 mL) in such a rate that the inner temperature did not exceed −5° C. After 10 min at this temperature, the solution was poured slowly onto ice-water (500 g), the precipitate was filtered and washed with cold water (2×200 mL) and cold diethyl ether (200 mL). The resulting solid was recrystallized from diethyl ether to give 4-methoxy-3-[4-(2,2,2-trifluoro-acetyl)-piperazin-1-yl]-benzenesulfonyl chloride as white powder (7.7 g; 41%), MS, MH$^+$ 387, m. p. 125–127.3° C.

Step 3:

2,2,2-Trifluoro-1-{4-[2-methoxy-5-(naphthalene-1-sulfonyl)-phenyl]-piperazin-1-yl}-ethanone

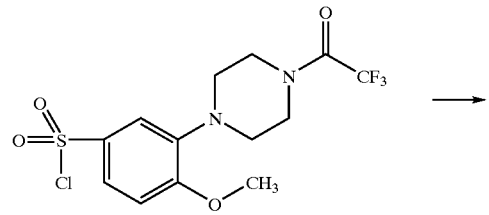

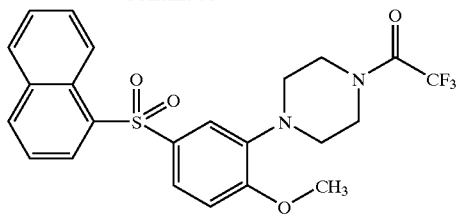

To a solution of 4-methoxy-3-[4-(2,2,2-trifluoro-acetyl)-piperazin-1-yl]-benzenesulfonyl chloride (0.19 g; 0.5 mmol) in THF (0.5 mL) at 0° C. under argon atmosphere was added dropwise a solution of 1-naphthylmagnesium bromide in THF (0.5M, 2 mL; 1 mmol). After stirring at this temperature for 1 h, a saturated solution of ammonium chloride was added and the mixture was extracted into ethyl acetate (20 mL). The organic phase was dried (Na$_2$SO$_4$) and concentrated in vacuo and the residue was purified by column chromatography on silica gel (eluting with hexane-ethyl acetate (7:3, v/v) to give 2,2,2-trifluoro-1-{4-[2-methoxy-5-(naphthalene-1-sulfonyl)-phenyl]-piperazin-1-yl}-ethanone (1) as a white solid (0.110 g; 47%), MS, MH$^+$ 479.

Similarly following Step 3, but replacing naphthylmagnesium bromide with the appropriate aryl magnesium bromides the following compounds were prepared:

2,2,2-trifluoro-1-{4-[2-methoxy-5-(naphthalene-2-sulfonyl)-phenyl]-piperazin-1-yl}-ethanone (2) as a white solid, MS, MH+ 479;

1-{4-[5-(4-chloro-benzenesulfonyl)-2-methoxy-phenyl]-piperazin-1-yl}-2,2,2-trifluoro-ethanone (3) as a white solid, MS, MH$^+$ 463;

1-{4-[5-(3-chloro-benzenesulfonyl)-2-methoxy-phenyl]-piperazin-1-yl}-2,2,2-trifluro-ethanone (4) as a white solid, MS, MH$^+$ 463;

1-{4-[5-(3,5-dichloro-benzenesulfonyl)-2-methoxy-phenyl]-piperazin-1-yl}-2,2,2-trifluro-ethanone (5) as a white solid, MS, MH$^+$ 497,498;

1-{4-[5-(4-methoxy-benzenesulfonyl)-2-methoxy-phenyl]-piperazin-1-yl}-2,2,2-trifluro-ethanone (6) as a white solid, MS, MH$^+$ 459; or 1-{4-[5-(3-fluoro-benzenesulfonyl)2-methoxyphenyl]piperazin-1-yl}2,2,2-trifluoro-ethanone (7) as a white solid, MS, MH$^+$ 447.

Step 4

1-[2-Methoxy-5-(naphthalene-1-sulfonyl)-phenyl]-piperazine

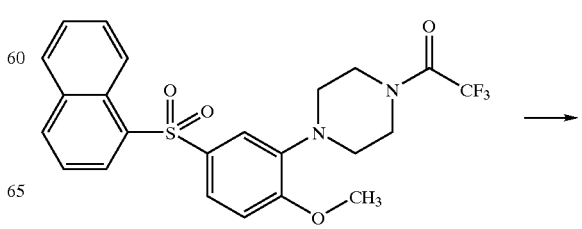

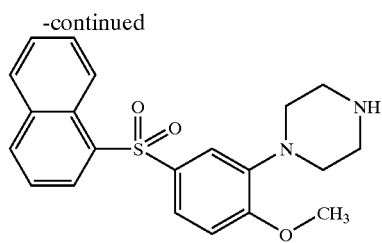

A solution of 6N NaOH (0.5 mL) was added to a suspension of 2,2,2-trifluoro-1-{4-[2-methoxy-5-(naphthalene-1-sulfonyl)-phenyl]-piperazin-1-yl}-ethanone (1) (0.110 g; 0.23 mmol ) in methanol. After stirring at 80° C. for 10 min water was added (10 ml) and the mixture was extracted into ethyl acetate (20 ml). The organic phase was dried ($Na_2SO_4$) and concentrated in vacuo to give 1-[2-methoxy-5-(naphthalene-1-sulfonyl)-phenyl]-piperazine (101) as a white solid (0.060 g , 68%), MS, $MH^+$ 383. The hydrochloride salt was prepared from ethanol-hydrogen chloride, m. p. 154–158° C.

Similarly replacing 2,2,2-trifluoro-1-{4-[2-methoxy-5-(naphthalene-1-sulfonyl)-phenyl]-piperazin-1-yl}-ethanone (1) with the appropriate trifluorothanone compounds of Step 3 the following compounds were prepared.

2,2,2-trifluoro-1-{4-[2-methoxy-5-(naphthalene-2-sulfonyl)-phenyl]-piperazin-1-yl}-ethanone (2) afforded 1-[2-methoxy-5-(naphthalene-2-sulfonyl)-phenyl]-piperazine (102) MS, $MH^+$ 383, m. p. 279.9–283.3° C.

1-{4-[5-(4-chloro-benzenesulfonyl)-2-methoxy-phenyl]-piperazin-1-yl}-2,2,2-trifluoro-ethanone (3) afforded 1-[5-(4-chloro-benzenesulfonyl)-2-methoxy-phenyl]-piperazine (103) MS, $MH^+$ 367, m. p. 263.4–272.1° C.

1-{4-[5-(3-chloro-benzenesulfonyl)-2-methoxy-phenyl]-piperazin-1-yl}-2,2,2-trifluoro-ethanone (4) afforded 1-[5-(3-chloro-benzenesulfonyl)-2-methoxy-phenyl]-piperazine (104) MS, $MH^+$ 367, m. p. 265–266.3° C.

1-{4-[5-(3,5-dichloro-benzenesulfonyl)-2-methoxy-phenyl]-piperazin-1-yl}-2,2,2-trifluoro-ethanone (5) afforded 1-[5-(3,5-dichloro-benzenesulfonyl)-2-methoxy-phenyl]-piperazine (105) MS, $MH^+$ 402, m. p. 245.9–246.2° C.

1-{4-[5-(4-methoxy-benzenesulfonyl)-2-methoxy-phenyl]-piperazin-1-yl}-2,2,2-trifluoro-ethanone (6) 1-[5-(4-methoxy-benzenesulfonyl)-2-methoxy-phenyl]-piperazine (106) MS, $MH^+$ 363, m. p. 260.1–260.6° C.

1-{4-[5-(3-fluoro-benzenesulfonyl)2-methoxyphenyl]piperazin-1-yl}2,2,2-trifluoro-ethanone (7) afforded 1-[5-(3-fluoro-benzenesulfonyl)-2-methoxy-phenyl]-piperazine (107) MS, $MH^+$ 351, m. p. 246.0–250.1° C.

Example 2

1-[5-(4-Methoxy-benzenesulfonyl)2-methoxyphenyl]piperazine

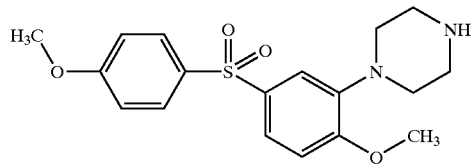

Alternate preparation without isolation of intermediate:

To a solution of 4-methoxy-3-[4-(2,2,2-trifluoro-acetyl)-piperazin-1-yl]-benzenesulfonyl chloride (0.19 g), prepared as in Example 1 Step 2, in THF (0.5 ml) at 0° C. under argon atmosphere was added dropwise a solution of 4-methoxyphenylmagnesium bromide in THF (0.5M, 2 ml; 1 mmol). After stirring at this temperature for 1 h. A solution of 6N NaOH (0.5 ml) was added and the reaction mixture was stirred at ambient temperature for 20 h. Water was added (10 ml) and the mixture was extracted into ethyl acetate (20 ml). The organic phase was dried ($Na_2SO_4$) and concentrated in vacuo to give 1-[5-(4-methoxy-benzenesulfonyl)2-methoxy-phenyl]piperazine as a white solid (0.65 g, 36%), MS, $MH^+$ 363.

Similarly but replacing phenylmagnesium bromide for methoxyphenylmagnesium bromide, 1-(5-benzenesulfonyl-2-methoxy-phenyl)-piperazine, (201) MS, $MH^+$ 333, m. p. 270.0–273.0° C., was prepared.

Example 3

4-[5-(4-Chloro-benzenesulfonyl)2methoxy-phenyl]piperidine

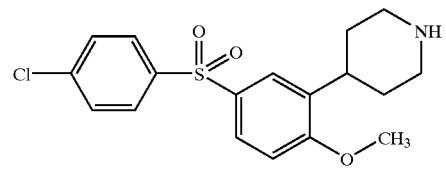

Step 1:
1-{4-[5-(4-Chloro-benzenesulfonyl)-2-methoxy-phenyl]-piperidin-1-yl}-2,2,2-trifluoro-ethanone

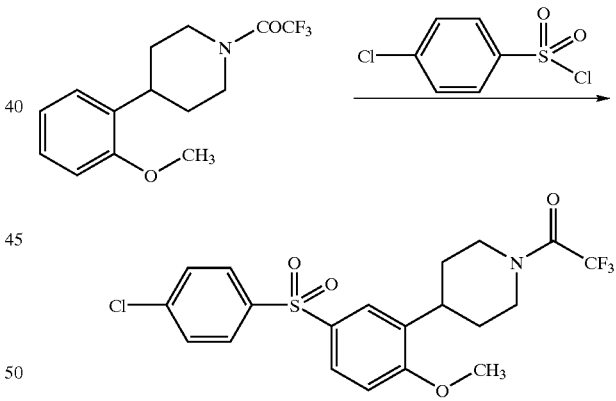

To a solution of 2,2,2-trifluoro-1-[4-(2-methoxyphenyl) piperidin-1-yl] ethanone (0.285 g; 1 mmol), prepared as in Example 1 Step 1, and 4-chlorobenzenesulfonyl chloride (0.210 g; 1 mmol) in 1,2-dichloroethane (2 mL) at 0° C. under nitrogen atmosphere was added, in small portions, aluminum chloride (0.134 g; 1 mmol), and the mixture was refluxed for 18 h. After cooling to 0° C. a solution of 2N HCl (2 mL) was added and the mixture was extracted into dichloromethane (20 mL). The organic phase was dried ($Na_2SO_4$), concentrated in vacuo and the residue was purified by column chromatography on silica gel (eluting with hexane-ethyl acetate (7:3, v/v) to give 1-{4-[5-(4-chloro-benzenesulfonyl)2-methoxyphenyl]piperidin-1-yl}2,2,2-trifluoro-ethanone (31) as white solid (0.077 g; 17%).

Step 2:
4-[5-(4-Chloro-benzenesulfonyl)2methoxy-phenyl]piperidine

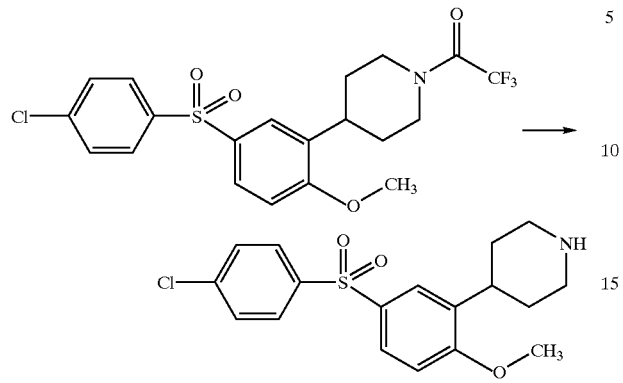

To a suspension of 1-{4-[5-(4-chloro-benzenesulfonyl)2-methoxyphenyl]piperidin-1-yl}-2,2,2-trifluoro-ethanone (31) (77 mg) in methanol (2 mL), a solution of 6N NaOH (0.5 mL) was added. After stirring at 80° C. for 10 min, water was added (10 ml) and the mixture was extracted into ethyl acetate (20 ml). The organic phase was dried ($Na_2SO_4$) and concentrated in vacuo to give 4-[5-(4-chloro-benzenesulfonyl)2methoxy-phenyl] piperidine (301) as a white solid (0.054 g ), MS, $MH^+$ 365. The hydrochloride salt was prepared from ethanol-hydrogen chloride, m.p. 235.5–236.0° C.

Example 4

1-[5-(4-Fluoro-naphthalene-1-sulfonyl)2-methoxyphenyl]piperazine

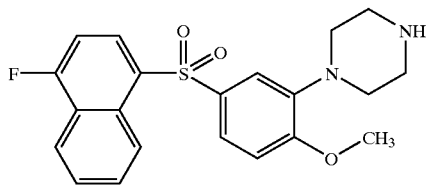

To a solution of 4-methoxy-3-[4-(2,2,2-trifluoro-acetyl) piperazin-1-yl]bezenesulfonyl chloride (0.19 g; 0.5 mmol), prepared as in Example 1 Step 2, in THF (0.5 mL) at ambient temperature under argon atmosphere was added dropwise a solution of 4-fluoro-1-naphthylmagnesium bromide in THF (0.25 M, 4 mL; 1 mmol). After stirring at this temperature for 1 h a saturated solution of ammonium chloride was added and the mixture was extracted into ethyl acetate (20 mL). The organic phase was dried ($Na_2SO_4$) and concentrated in vacuo .The residue was dissolved in dioxane (2 mL) and a solution of 6N NaOH (0.5 mL) was added. After stirring at ambient temperature for 1 h water was added (10 ml) and the mixture was extracted into ethyl acetate (20 ml). The organic phase was extracted into 2N aqueous HCl. The aqueous layer was adjusted with 6N NaOH solution to pH 14 and extracted with ethyl acetate. The organic phase was dried ($Na_2SO_4$) and concentrated in vacuo to give the 1-[5-(4-fluoro-naphthalene-1-sulfonyl)2-methoxyphenyl] piperazine (401) as a white solid (0.060 g; 30%). The hydrochloride salt was prepared from ethanol-hydrogen chloride, m. p. 155.0–159.0° C.

Similarly replacing 4-fluoro-1-naphthylmagnesium bromide with 3,4-dichloro-1-phenyl magnesium bromide, 1-[5-(3,4-dichloro-benzenesulfonyl)-2-methoxy-phenyl]-piperazine (402), MS, $MH^+$ 401, m.p. 260.0–263.0, was prepared.

Example 5

1-[2-Methoxy-5-(4-methoxy-naphthalene-1-sulfonyl)phenyl]piperazine

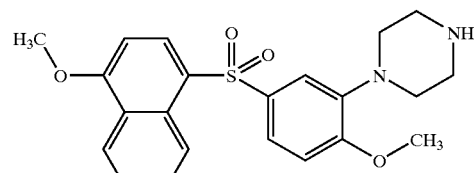

To a solution of 1-[5-(4-fluoro-naphthalene-1-sulfonyl)2-methoxyphenyl] piperazine (0.050 g; 0.12 mmol) prepared in example 4 in methanol (2 mL) was added a solution of 6N NaOH (0.5 mL). After stirring at 80° C. for 30 min water was added (10 ml) and the mixture was extracted into ethyl acetate (20 mL). The organic phase was extracted into 2N aqueous HCl. The aqueous layer was adjusted with 6N NaOH solution to pH 14 and extracted with ethyl acetate. The organic phase was dried ($Na_2SO_4$) and concentrated in vacuo to give 1-[2-methoxy-5-(4-methoxy-naphthalene-1-sulfonyl)phenyl] piperazine (501) as a white solid (0.043 g; 88%). The hydrochloride salt was prepared from ethanol-hydrogen chloride, m. p. 240.243.0° C.

Example 6

Composition for Oral Administration

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Example 7

Composition for Oral Administration

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Example 8

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavouring | 0.035 mL |
| Colourings | 0.5 mg |
| Distilled water | q.s. to 100 mL |

The ingredients are mixed to form a suspension for oral administration.

Example 9

Parenteral Formulation (IV)

| Ingredient | % wt./wt. |
| --- | --- |
| Active ingredient | 0.25 g |
| Sodium Chloride | qs to make isotonic |
| Water for injection to | 100 mL |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Example 10

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Example 11

Topical Formulation

| Ingredients | grams |
| --- | --- |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Example 12

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

Example 13

Radioligand Binding Studies

The binding activity of compounds of this invention in vitro was determined as follows.

Duplicate determinations of ligand affinity are made by competing for binding of [3H]LSD in cell membranes derived from HEK293 cells stably expressing recombinant human 5-HT6 receptor.

All determinations are made in assay buffer containing 50 mM Tris-HCl, 10 mM MgSO4, 0.5 mM EDTA, 1 mM ascorbic acid, pH 7.4 at 37° C., in a 250 microliter reaction volume. Assay tubes containing [3H] LSD (5 nM), competing ligand, and membrane are incubated in a shaking water bath for 60 min. at 37° C., filtered onto Packard GF-B plates (pre-soaked with 0.3% PEI) using a Packard 96 well cell harvester and washed 3 times in ice cold 50 mM Tris-HCl. Bound [3H] LSD is determined as radioactive counts per minute using Packard TopCount.

Displacement of [3H]LSD from the binding sites was quantified by fitting concentration-binding data to a 4-parameter logistic equation:

$$\text{binding} = \text{basal} + \left( \frac{B\text{max} - \text{basal}}{1 + 10^{-Hill(\log[\text{ligand}] - \log IC_{50})}} \right)$$

where Hill is the Hill slope, [ligand] is the concentration of competing radioligand and IC50 is the concentration of radioligand producing half-maximal specific binding of radioligand. The specific binding window is the difference between the Bmax and the basal parameters.

Proceeding as in Example 13, compounds of Formula (I) were tested and found to be selective 5-HT6 antagonists.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the Formula (I):

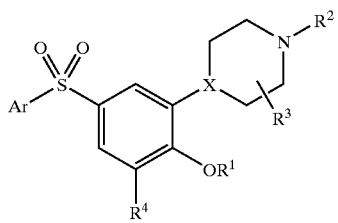

Formula (I)

wherein:
Ar is an optionally substituted aryl group selected from naphthyl and phenyl;
X is —CH— or —N—;
$R^1$ is $(C_1-C_6)$alkyl;
$R^2$ and $R^3$ are each independently in each occurrence hydrogen or $(C_1-C_6)$alkyl;
$R^4$ is hydrogen, or $R^1$ and $R^4$ together may form a —CH=CH—, —CH$_2$—CH$_2$—, —CH$_2$— CH$_2$—CH$_2$—, —O—CH$_2$—, or —O—CH$_2$—CH$_2$— group;
or pharmaceutically acceptable salts or solvates thereof.

2. The compound of claim 1, wherein X is —N—.

3. The compound of claim 2, wherein Ar is unsubstituted naphthyl.

4. The compound of claim 3, wherein $R^1$ is methyl, and $R^2$ and $R^3$ are hydrogen, named 1-[2-methoxy-4-(naphthalene-1-sulfonyl)-pheny-1]-piperazine.

5. The compound of claim 3, wherein $R^1$ is methyl, and $R^2$ and $R^3$ are hydrogen, named 1-[2-methoxy-4-(naphthalene-2-sulfonyl)-phenyl-1]-piperazine.

6. The compound of claim 2, wherein Ar is substituted naphthyl wherein the substitutents are selected from $(C_1-C_6)$ alkyl, halogen, haloalkyl, $(C_1-C_6)$alkoxy, cyano, nitro, amino, and alkylsulfonyl.

7. The compound of claim 6, wherein $R^1$ is methyl, and $R^2$ and $R^3$ are hydrogen, named 1-[5-(4-fluoro-naphthalene-1-sulfonyl)2-methoxyphenyl]piperazine.

8. The compound of claim 6, wherein $R^1$ is methyl, and $R^2$ and $R^3$ are hydrogen, named 1-[2-methoxy-5-(4-methoxy-naphthalene-1-sulfonyl)phenyl]piperazine.

9. The compound of claim 2, wherein Ar is unsubstituted phenyl.

10. The compound of claim 9, wherein $R^1$ is methyl, and $R^2$ and $R^3$ are hydrogen, named 1-(5-benzenesulfonyl-2-methoxy-phenyl)-piperazine.

11. The compound of claim 2, wherein Ar is a phenyl group wherein the substituent is independently selected from halogen, haloalkyl, $(C_1-C_6)$alkoxy, cyano, nitro, and alkylsulfonyl.

12. The compound of claim 11, wherein $R^1$ is methyl, and $R^2$ and $R^3$ are hydrogen, named 1-[5-(4-chloro-benzenesulfonyl)-2-methoxy-phenyl]-piperazine.

13. The compound of claim 11, wherein $R^1$ is methyl, and $R^2$ and $R^3$ are hydrogen, named 1-[5-(3-chloro-benzenesulfonyl)-2-methoxy-phenyl]-piperazine.

14. The compound of claim 11, wherein $R^1$ is methyl, and $R^2$ and $R^3$ are hydrogen, named 1-[5-(3,5-dichlorobenzenesulfonyl)-2-methoxy-phenyl]-piperazine.

15. The compound of claim 11, wherein $R^1$ is methyl, and $R^2$ and $R^3$ are hydrogen, named 1-[5-(4-methoxy-benzenesulfonyl)-2-methoxy-phenyl]-piperazine.

16. The compound of claim 11, wherein $R^1$ is methyl, and $R^2$ and $R^3$ are hydrogen, named 1-[5-(3-fluoro-benzenesulfonyl)-2-methoxy-phenyl]-piperazine.

17. The compound of claim 11, wherein $R^1$ is methyl, and $R^2$ and $R^3$ are hydrogen, named 1-[5-(3,4-dichlorobenzenesulfonyl)-2-methoxy-phenyl]-piperazine.

18. The compound of claim 1, wherein X is —CH—.

19. The compound of claim 18, wherein Ar is phenyl unsubstituted or mono-, di- or tri-substituted with a group independently selected from halogen, $(C_1-C_6)$alkoxy, cyano, nitro, and alkylsulfonyl.

20. The compound of claim 19, wherein $R^1$ is methyl, and $R^2$ and $R^3$ are hydrogen, named 4-[5-(4-chloro-benzenesulfonyl)2-methoxy-phenyl]piperidine.

21. A pharmaceutical composition comprising a therapeutically effective amount of at least one compound of claim 1 in admixture with at least one pharmaceutically acceptable carrier.

22. A method of treating a subject that has a disease state selected from schizophrenia, depression, and cognitive memory disorders, wherein said method comprises administering to said subject a therapeutically effective amount of the compound of claim 1.

23. A process for preparing a compound as claimed in claim 1 which comprises:

i) reacting a compound having a general Formula (b)

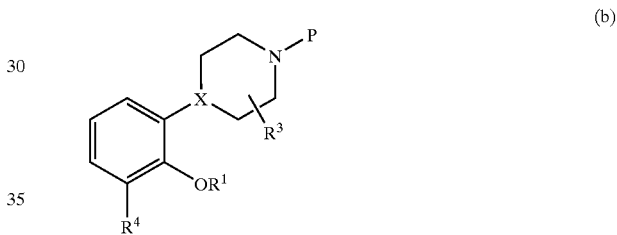

(b)

wherein P is a protecting group and $R^1$, $R^3$, and $R^4$ are as defined in claim 1, with a compound of general formula Ar—S(O)$_2$—Cl, wherein Ar aryl, ii) deprotection; and iii) optional alkylation to provide a compound of Formula (I)

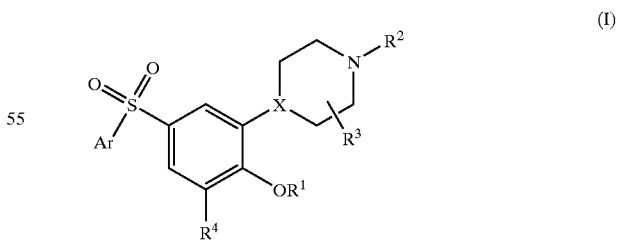

(I)

wherein Ar, X, $R^1$, $R^2$, $R^3$, and $R^4$ are as defined in claim 1.

24. A process for preparing a compound as claimed in claim 1 which comprises:

i) reacting a compound having a general Formula (b)

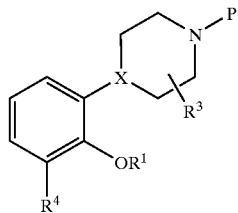
(b)

wherein P is a protecting group and $R^1$, $R^2$, $R^3$, and $R^4$ are as defined in claim 1
  with a compound $S(O)_2$—Cl,
  ii) reaction with a Grignard reagent of general formula ArMgHal, wherein Ar is as defined in claim 1 and 11a1 is a halide,
  ii) deprotection, and
  iii) optional alkylation
  to provide a compound of Formula (I)

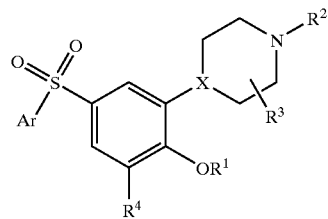
(I)

wherein Ar, X, $R^1$, $R^2$, $R^3$, and $R^4$ are as defined in claim 1.

* * * * *

UNITED STATES PATENT AND TRADEMARK OFFICE
CERTIFICATE OF CORRECTION

PATENT NO.    : 6,825,202 B2
DATED         : November 30, 2004
INVENTOR(S)   : Jacob Berger et al.

It is certified that error appears in the above-identified patent and that said Letters Patent is hereby corrected as shown below:

Column 21,
Lines 29-30, "1-[2-methoxy-4-(naphthalene-1-sulfonyl)-pheny-l]-piperazine."
should read -- 1-[2-methoxy-5-(naphthalene-1-sulfonyl)-phenyl]-piperazine. --;
Lines 32-33, "1-[2-methoxy-4-(naphthalene-2-sulfonyl)-phenyl-l]-piperazine."
should read -- 1-[2-methoxy-5-(naphthalene-2-sulfonyl)-phenyl]-piperazine. --;

Column 23,
Line 17, "claim 1 and 11a1 is a halide," should read -- claim 1 and Hal is a halide, --.

Signed and Sealed this

Seventeenth Day of May, 2005

JON W. DUDAS
*Director of the United States Patent and Trademark Office*